(12) United States Patent
Baudy

(10) Patent No.: US 7,879,826 B2
(45) Date of Patent: Feb. 1, 2011

(54) DERIVATIVES OF [2-(8,9-DIOXO-2,6-DIAZABICYCLO[5.2.0]NON-1(7)-EN-2-YL)ALKYL]PHOSPHONIC ACID AND METHODS OF MAKING THEM

(75) Inventor: Reinhardt Bernhard Baudy, Hellertown, PA (US)

(73) Assignee: Wyeth LLC, Madison, NJ (US)

( * ) Notice: Subject to any disclaimer, the term of this patent is extended or adjusted under 35 U.S.C. 154(b) by 852 days.

(21) Appl. No.: 11/758,459

(22) Filed: Jun. 5, 2007

(65) Prior Publication Data

US 2007/0244100 A1 Oct. 18, 2007

Related U.S. Application Data

(63) Continuation of application No. 11/244,599, filed on Oct. 6, 2005, now Pat. No. 7,268,123.

(60) Provisional application No. 60/617,023, filed on Oct. 8, 2004.

(51) Int. Cl.
- A61P 25/00 (2006.01)
- A61K 31/675 (2006.01)
- C07D 223/00 (2006.01)

(52) U.S. Cl. ........................ 514/80; 540/542
(58) Field of Classification Search ................ 514/80; 540/542

See application file for complete search history.

(56) References Cited

U.S. PATENT DOCUMENTS

| 5,168,103 A | 12/1992 | Kinney et al. | 514/221 |
| 2005/0004080 A1 | 1/2005 | Baudy et al. | 514/80 |

FOREIGN PATENT DOCUMENTS

| EP | 0 496 561 A2 | 7/1992 |
| EP | 0 496 561 A3 | 7/1992 |
| EP | 0 496 561 B1 | 3/1995 |

OTHER PUBLICATIONS

Brandt, M. R. et al. "Antinociceptive Effects of δ-Opioid Agonists in Rhesus Monkeys: Effects on Chemically Induced Thermal Hypersensitivity," *J. Pharmacol. Exper. Ther.*, 2001, 296, 939-946.
*Diagnostic and Statistical Manual of Mental Disorders*, 4th edition, Washington, DC, American Psychiatric Association (1994), pp. 273-315, 317-391 and 393-445.
Eliel, E. L., *Stereochemistry of Carbon Compounds*, McGraw Hill, NY (1962) Ch. 4, pp. 46-87.
Jacques, J. et al., *Enantiomers, Racemates and Resolutions*, Wiley Interscience, NY (1981) pp. 251-434.

Mendell, J. R. et al., "Painful Sensory Neuropathy," *N. Engl. J. Med.*, Mar. 27, 2003, 348(13), pp. 1243-1255.
*Physicians' Desk Reference*, 55th Edition, 2001, published by Medical Economics Co., Inc., Montvale, NJ, Section 3, pp. 201-216.
*Remington's Pharmaceutical Sciences*, 17th Ed., Gennaro, A. R. (Ed.), Mack Publishing Company, Easton, PA (1985) pp. 1409-1677.
Wilen, S.H., *Tables of Resolving Agents and Optical Resolutions*, pp. 268-298, E.L. Eliel, Ed., University of Notre Dame Press, Notre Dame, IN 1972.
Wilen, S.H., et al., "Strategies in optical resolutions," *Tetrahedron*, 33, pp. 2725-2736, 1977.
Brown et al., "N-Methyl-D-Aspartate Receptor (NMDA) Antagonsists as Potential Pain Therapeutics," *Current Topics in Medicinal Chemistry*, 2006, 6(8), 749-770.

*Primary Examiner*—Brenda L Coleman
(74) *Attorney, Agent, or Firm*—Joel Silver

(57) ABSTRACT

Compounds of formula (I) or pharmaceutically acceptable salts thereof are provided:

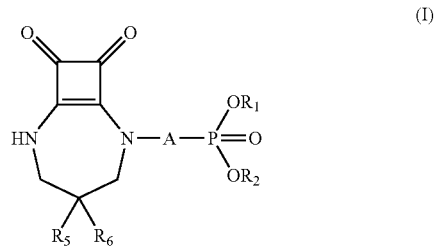

(I)

wherein:
A is alkylenyl of 1 to 4 carbon atoms, or alkenylenyl of 2 to 4 carbon atoms;
$R_1$ and $R_2$ are, independently, hydrogen or a $C_5$ to $C_7$ aryl optionally substituted with 1 to 2 substituents, independently, selected from the group consisting of —C(O)$R_3$, halogen, cyano, nitro, hydroxyl, $C_1$-$C_6$ alkyl, and $C_1$-$C_6$ alkoxy,
with the proviso that at least one of $R_1$ and $R_2$ is not hydrogen;
$R_3$ is, independently, hydrogen, —O$R_4$, alkyl, aryl, or heteroaryl;
$R_4$ is hydrogen, alkyl, aryl, or heteroaryl;
$R_5$ and $R_6$ are, independently, hydrogen, alkyl, hydroxyl, alkoxy, or $C_5$ to $C_7$ aryl;
wherein any $R_3$ to $R_6$ group having an aryl or heteroaryl moiety can optionally be substituted on the aryl or heteroaryl moiety with 1 to about 5 substituents, independently, selected from the group consisting of halogen, cyano, nitro, hydroxyl, $C_1$-$C_6$ alkyl, and $C_1$-$C_6$ alkoxy.

Methods of making these compounds as well as methods using the compounds for treating a variety of conditions are also disclosed.

1 Claim, No Drawings

DERIVATIVES OF [2-(8,9-DIOXO-2,6-DIAZABICYCLO[5.2.0]NON-1(7)-EN-2-YL) ALKYL]PHOSPHONIC ACID AND METHODS OF MAKING THEM

CROSS-REFERENCE TO RELATED APPLICATIONS

This application is a continuation of U.S. Application Ser. No. 11/244,599, filed Oct. 6, 2005 (now allowed), which claims the benefit of U.S. Application Ser. No. 60/617,023, filed Oct. 8, 2004, the entire disclosures of which are incorporated herein by reference.

BACKGROUND OF THE INVENTION

The present invention relates to derivatives of [2-(8,9-dioxo-2,6-diazabicyclo[5.2.0]non-1(7)-en-2-yl)alkyl]phosphonic acid and methods of making them. The compounds of the present invention are particularly useful as N-methyl-D-aspartate (NMDA) receptor antagonists.

Glutamate and aspartate play dual roles in the central nervous system as essential amino acids and as the principal excitatory neurotransmitters. There are at least four classes of excitatory amino acid receptors: NMDA, AMPA (2-amino-3-(methyl-3-hydroxyisoxazol-4-yl)propanoic acid), kainate, and metabotropic receptors. These excitatory amino acid receptors regulate a wide range of signaling events that impact physiological brain functions. For example, activation of the NMDA receptor has been shown to be the central event that leads to excitotoxicity and neuronal death in many disease states, as well as a result of hypoxia and ischaemia following head trauma, stroke, and following cardiac arrest. It is also known that the NMDA receptor plays a major role in the synaptic plasticity that underlies many higher cognitive functions, such as memory and learning, certain nociceptive pathways, and in the perception of pain. In addition, certain properties of NMDA receptors suggest that they may be involved in the information-processing in the brain that underlies consciousness itself.

NMDA receptors are localized throughout the central nervous system. NMDA receptors are ligand-gated cation channels that modulate sodium, potassium, and calcium ions flux when they are activated by glutamate in combination with glycine. Structurally, the NMDA receptor is thought to be comprised of heteromultimeric channels containing two major subunits designated as NR1 and NR2. These subunits contain a glycine binding site, a glutamate binding site, and a polyamine binding site. For the NR1 subunit, multiple splice variants have been identified, whereas for the NR2 subunit, four individual subunit types (NR2A, NR2B, NR2C, and NR2D) have been identified. The NMDA receptor also contains an $Mg^{++}$ binding site located inside the pore of the ionophore of the NMDA receptor/channel complex, which blocks the flow of ions.

Substantial preclinical and clinical evidence indicates that inhibitors of the NMDA receptor have therapeutic potential for treating numerous disorders. Disorders believed to be responsive to inhibition of NMDA receptors include cerebral vascular disorders, such as cerebral ischemia (e.g., stroke) or cerebral infarction resulting in a range of conditions, such as thromboembolic or hemorrhagic stroke, or cerebral vasospasm; cerebral trauma; muscular spasm; and convulsive disorders, such as epilepsy or status epilepticus. NMDA receptor antagonists may also be used to prevent tolerance to opiate analgesia or to help control symptoms of withdrawal from addictive drugs.

Screening of compounds in recent years have identified a number of NMDA receptor antagonists that have been used in animal and clinical human studies to demonstrate proof of concept for the treatment of a variety of disorders. The difficulty with demonstrating clinical utility of NMDA receptor antagonists has generally been the antagonists' lack of NMDA receptor subtype selectivity and/or biological activity, when dosed orally. Thus, the search for NMDA receptor antagonists that are subtype-selective and/or orally efficacious continues.

SUMMARY OF THE INVENTION

In one embodiment, the invention provides compounds of formula (I) or a pharmaceutically acceptable salt thereof:

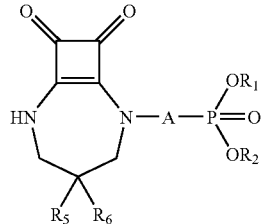

(I)

wherein:

A is alkylenyl of 1 to 4 carbon atoms or alkenylenyl of 2 to 4 carbon atoms;

$R_1$ and $R_2$ are, independently, hydrogen or a $C_5$ to $C_7$ aryl optionally substituted with 1 to 2 substituents, independently, selected from the group consisting of $—C(O)R_3$, halogen, cyano, nitro, hydroxyl, $C_1$-$C_6$ alkyl, and $C_1$-$C_6$ alkoxy;

with the proviso that at least one of $R_1$ and $R_2$ is not hydrogen;

$R_3$ is hydrogen, $—OR_4$, alkyl, aryl, or heteroaryl, and $R_4$ is hydrogen, alkyl, aryl, or heteroaryl, $R_5$ and $R_6$ are, independently, hydrogen, alkyl, OH, alkoxy, or $C_5$ to $C_7$ aryl;

wherein any $R_3$ to $R_6$ group having an aryl or heteroaryl moiety may optionally be substituted on the aryl or heteroaryl moiety with 1 to about 5 substituents, independently, selected from the group consisting of halogen, cyano, nitro, hydroxyl, $C_1$-$C_6$ alkyl, and $C_1$-$C_6$ alkoxy.

In some further embodiments, the invention provides compounds of formula (II) or pharmaceutically acceptable salt thereof:

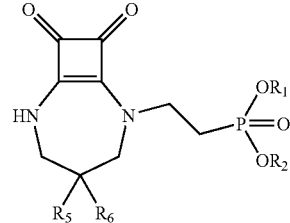

(II)

wherein:

$R_1$ and $R_2$ are, independently, hydrogen or

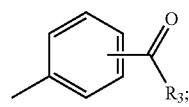

with the proviso that at least one of $R_1$ and $R_2$ is not hydrogen;

$R_3$ is hydrogen, $—OR_4$, alkyl, aryl, or heteroaryl, $R_4$ is hydrogen, alkyl, aryl, or heteroaryl, $R_5$ and $R_6$ are, independently, hydrogen, alkyl, OH, alkoxy, or $C_5$ to $C_7$ aryl;

wherein any $R_3$ to $R_6$ group having an aryl or heteroaryl moiety may optionally be substituted on the aryl or heteroaryl moiety with 1 to about 5 substituents, independently, selected from the group consisting of halogen, cyano, nitro, hydroxyl, $C_1$-$C_6$ alkyl, and $C_1$-$C_6$ alkoxy.

In some further embodiments, the invention includes compounds of formula (III) or pharmaceutically acceptable salt thereof:

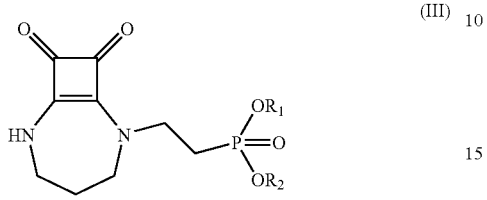
(III)

wherein:

$R_1$ and $R_2$ are, independently, hydrogen or

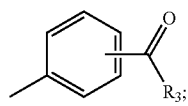

with the proviso that at least one of $R_1$ and $R_2$ is not hydrogen;

$R_3$ is hydrogen, alkyl, aryl, or heteroaryl, and wherein any aryl or heteroaryl moiety may optionally be substituted on the aryl or heteroaryl moiety with 1 to about 5 substituents, independently, selected from the group consisting of halogen, cyano, nitro, hydroxyl, $C_1$-$C_6$ alkyl, and $C_1$-$C_6$ alkoxy.

In other embodiments, the invention provides a compound of formula (III) or pharmaceutically acceptable salt thereof:

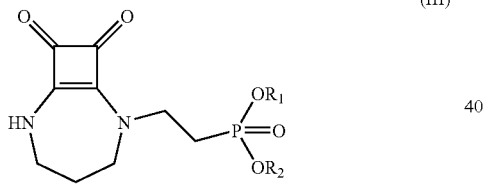
(III)

wherein:

$R_1$ and $R_2$ are, independently, hydrogen or

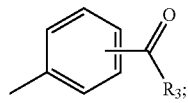

with the proviso that at least one of $R_1$ and $R_2$ is not hydrogen;

$R_3$ is —$OR_4$, $R_4$ is hydrogen, alkyl, aryl, or heteroaryl; and wherein any aryl or heteroaryl moiety may optionally be substituted on the aryl or heteroaryl moiety with 1 to about 5 substituents, independently, halogen, cyano, nitro, hydroxyl, $C_1$-$C_6$ alkyl, or $C_1$-$C_6$ alkoxy.

In still other embodiments, the invention provides a composition comprising at least one compound of formula (I), (II), (III), and pharmaceutically acceptable salts thereof, described above.

In some further embodiments, the invention provides methods of making the compounds of formula (I), (II), (III), and pharmaceutically acceptable salts thereof, wherein the method comprises the steps of:

reacting a compound of formula (2)

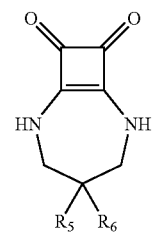
(2)

or a pharmaceutically acceptable salt thereof, with a compound of formula (3)

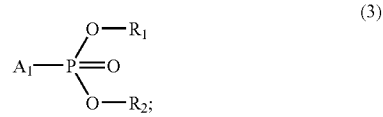
(3)

wherein $A_1$ is alkenyl having 2 to 4 carbon atoms or alkynyl having 2-4 carbon atoms, under conditions effective to form a compound of formula (I), or a pharmaceutically acceptable salt thereof.

In some further embodiments, the invention provides methods for making a compound of formula (I), (II), (III), and pharmaceutically acceptable salts thereof, comprising the steps of:

treating a disubstituted diaminoalkane derivative of formula (6)

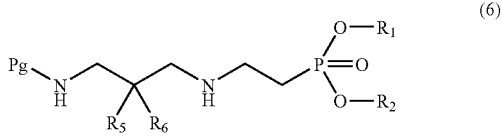
(6)

wherein Pg is a protecting group, with a dialkoxysquarate of formula (1)

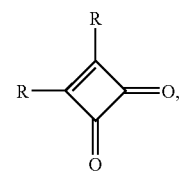
(1)

wherein R is alkoxy, preferably $C_1$-$C_4$ alkoxy, in a suitable solvent to yield a tri-substituted diaminoalkane derivative of formula (7)

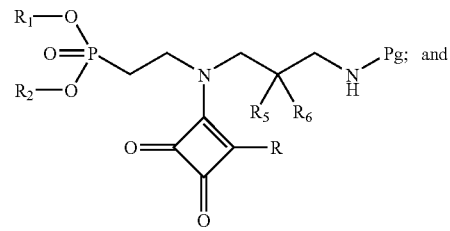

deprotecting and cyclizing the tri-substituted diaminoalkane derivative of formula (7) to produce a compound of formula (I).

In other embodiments, the invention provides a product made by any of the foregoing processes.

In other embodiments, the invention provides a pharmaceutical composition comprising a therapeutically effective amount of at least one compound of formula (I), (II), (III), and pharmaceutically acceptable salts thereof, described above.

In further embodiments, the invention provides methods for treating at least one condition in a mammal selected from the group consisting of cerebral vascular disorder selected from the group consisting of cerebral ischemia, cerebral infarction, cerebral vasospasm, and combinations thereof; cerebral trauma; muscular spasm; a convulsive disorder selected from the group consisting of epilepsy, status epilepticus, and combinations thereof; hypoglycemia; cardiac arrest; asphyxia anoxia; spinal chord injury, and combinations thereof, comprising the step of:

administering to said mammal in need thereof an effective amount of at least one compound of formula (I), (II), (III), and pharmaceutically acceptable salts thereof, described above.

In further embodiments, the invention provides methods for treating at least one condition in a mammal selected from the group consisting of glaucoma, diabetic end organ complications, and combinations thereof, comprising the step of:

administering to a mammal in need thereof an effective amount of at least one compound of formula (I), (II), (III), and pharmaceutically acceptable salts thereof, described above.

In further embodiments, the invention provides methods for treating at least one condition in a mammal selected from the group consisting of anxiety disorder; mood disorder; schizophrenia; schizophreniform disorder; schizoaffective disorder, and combinations thereof, comprising the step of:

administering to a mammal in need thereof an effective amount of at least one compound of formula (I), (II), (III), and pharmaceutically acceptable salts thereof, described above.

In further embodiments, the invention provides methods for treating at least one neurodegenerative disorder in a mammal selected from the group consisting of Parkinson's disease, Huntingdon's disease, Alzheimer's disease, amyotrophic lateral sclerosis, chronic dementia, cognitive impairment, and combinations thereof, comprising the step of:

administering to a mammal in need thereof an effective amount of at least one compound of formula (I), (II), (III), and pharmaceutically acceptable salts thereof, described above.

In further embodiments, the invention provides methods for treating at least one condition in a mammal selected from the group consisting of inflammatory diseases; fibromyalgia; complications from herpes zoster; prevention of tolerance to opiate analgesia; withdrawal symptoms from addictive drugs, and combinations thereof, comprising the step of:

administering to a mammal in need thereof an effective amount of at least one compound of formula (I), (II), (III), and pharmaceutically acceptable salts thereof, described above.

In further embodiments, the invention provides methods for treating pain in a mammal, comprising the step of:

administering to a mammal in need thereof an effective amount of at least one compound of formula (I), (II), (III), and pharmaceutically acceptable salts thereof, described above.

DETAILED DESCRIPTION OF THE INVENTION

This invention provides compounds of formula (I) or a pharmaceutically acceptable salt thereof:

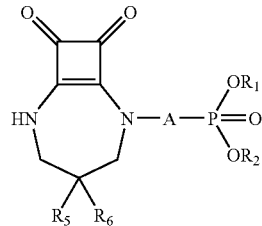

(I)

wherein:

A is alkylenyl of 1 to 4 carbon atoms or alkenylenyl of 2 to 4 carbon atoms;

$R_1$ and $R_2$ are, independently, hydrogen, or a $C_5$ to $C_7$ aryl optionally substituted with 1 to 2 substituents, independently, selected from the group consisting of —C(O)$R_3$, halogen, cyano, nitro, hydroxyl, $C_1$-$C_6$ alkyl, and $C_1$-$C_6$ alkoxy;

with the proviso that at least one of $R_1$ and $R_2$ is not hydrogen;

$R_3$ is hydrogen, —O$R_4$, alkyl, aryl, or heteroaryl, and $R_4$ is hydrogen, alkyl, aryl, or heteroaryl, $R_5$ and $R_6$ are, independently, hydrogen, alkyl, hydroxyl, alkoxy, or $C_5$ to $C_7$ aryl;

wherein any $R_3$ to $R_6$ group having an aryl or heteroaryl moiety may optionally be substituted on the aryl or heteroaryl moiety with 1 to about 5 substituents, independently, selected from the group consisting of halogen, cyano, nitro, hydroxyl, $C_1$-$C_6$ alkyl, and $C_1$-$C_6$ alkoxy.

In some further embodiments, the invention provides a compound of formula (II) or pharmaceutically acceptable salt thereof:

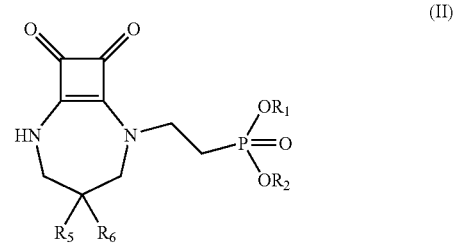

(II)

wherein:

$R_1$ and $R_2$ are, independently, hydrogen or

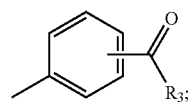

with the proviso that at least one of $R_1$ and $R_2$ is not hydrogen;

$R_3$ is hydrogen, —O$R_4$, alkyl, aryl, or heteroaryl, $R_4$ is hydrogen, alkyl, aryl, or heteroaryl, $R_5$ and $R_6$ are, independently, hydrogen, alkyl, OH, alkoxy, or $C_5$ to $C_7$ aryl;

wherein any $R_3$ to $R_6$ group having an aryl or heteroaryl moiety may optionally be substituted on the aryl or heteroaryl moiety with 1 to about 5 substituents, independently, selected from the group consisting of halogen, cyano, nitro, hydroxyl, $C_1$-$C_6$ alkyl, and $C_1$-$C_6$ alkoxy.

In some embodiments, the compounds of formula (II) are preferred compounds of formula (I).

In some further embodiments, the invention includes a compound of formula (III) or pharmaceutically acceptable salt thereof:

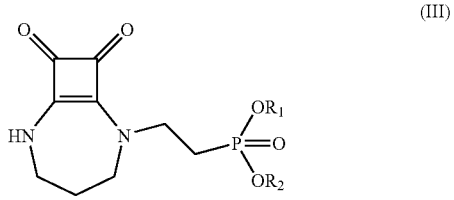

(III)

wherein:
$R_1$ and $R_2$ are, independently, hydrogen or

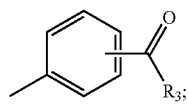

with the proviso that at least one of $R_1$ and $R_2$ is not hydrogen;

$R_3$ is hydrogen, alkyl, aryl, or heteroaryl; and wherein any aryl or heteroaryl moiety may optionally be substituted on the aryl or heteroaryl moiety with 1 to about 5 substituents, independently, selected from the group consisting of halogen, cyano, nitro, hydroxyl, $C_1$-$C_6$ alkyl, and $C_1$-$C_6$ alkoxy.

In certain embodiments, the compounds of formula (III) are preferred compounds of formula (II) and, in turn, preferred compounds of formula (I).

In other embodiments, the invention provides a compound of formula (III) or pharmaceutically acceptable salt thereof:

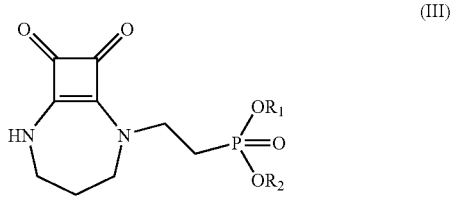

(III)

wherein:
$R_1$ and $R_2$ are, independently, hydrogen or

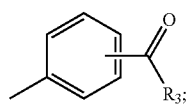

with the proviso that at least one of $R_1$ and $R_2$ is not hydrogen;

$R_3$ is —$OR_4$;

$R_4$ is hydrogen, alkyl, aryl, or heteroaryl; and wherein any aryl or heteroaryl moiety may optionally be substituted on the aryl or heteroaryl moiety with 1 to about 5 substituents, independently, halogen, cyano, nitro, hydroxyl, $C_1$-$C_6$ alkyl, or $C_1$-$C_6$ alkoxy.

In certain embodiments, the compounds of formula (III) are preferred compounds of formula (II) and, in turn, preferred compounds of formula (I).

In some embodiments, the compounds of formula (II) are preferred compounds of formula (I).

In certain embodiments, the compounds of formula (III) are preferred compounds of formula (II) and, in turn, preferred compounds of formula (I).

Unless otherwise indicated:

"Alkyl," as used herein, refers to an aliphatic hydrocarbon chain having 1 to 12 carbon atoms and includes, but is not limited to, straight or branched chains, such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms. In some embodiments of the invention, alkyl is preferably $C_1$ to $C_8$ and, more preferably, $C_1$ to $C_6$.

"Alkylenyl," as used herein, refers to a linking alkyl group (or bivalent alkyl group), e.g., —$CH_2$- or —$(CH_2)_2$—.

"Alkenyl," as used herein, refers to an aliphatic straight or branched hydrocarbon chain having 2 to 7 carbon atoms that contains 1 to 3 double bonds. Examples of alkenyl are straight or branched mono-, di-, or polyunsaturated groups, such as vinyl, prop-1-enyl, allyl, methallyl, but-1-enyl, but-2-enyl or but-3-enyl.

"Alkenylenyl," as used herein, refers to a linking alkenyl group (or a bivalent alkenyl group)

"Alkynyl," as used herein, refers to an aliphatic, straight or branched, hydrocarbon chain having 2 to 7 carbon atoms that may contain 1 to 3 triple bonds.

"Acyl," as used herein, refers to the group R—C(=O)— where R is an alkyl group of 1 to 6 carbon atoms. For example, a $C_2$ to $C_7$ acyl group refers to the group R—C(=O)— where R is an alkyl group of 1 to 6 carbon atoms.

"Alkanesulfonyl," as used herein, refers to the group R—S(O)$_2$— where R is an alkyl group of 1 to 6 carbon atoms.

"Aryl," as used herein, refers to an aromatic 5- to 13-membered mono- or bi-carbocyclic ring, such as phenyl or naphthyl. Preferably, groups containing aryl moieties are monocyclic having 5 to 7 carbon atoms in the ring. Heteroaryl means an aromatic 5- to 13-membered, carbon containing, mono- or bi-cyclic ring having one to five heteroatoms that, independently, may be selected from nitrogen, oxygen and sulfur. Preferably, groups containing heteroaryl moieties are monocyclic having 5 to 7 members in the ring where one to two of the ring members are selected, independently, from nitrogen, oxygen or sulfur. Groups containing aryl or heteroaryl moieties may optionally be substituted as defined below or unsubstituted.

"Aroyl," as used herein, refers to the group Ar—C(=O)— where Ar is aryl as defined above. For example, a $C_6$ to $C_{14}$ aroyl moiety refers to the group Ar—C(=O)— where Ar is an aromatic 5 to 13 membered carbocylic ring.

"Halogen," as used herein, means fluorine, chlorine, bromine or iodine.

"Substituted," as used herein, refers to a moiety, such as an aryl or heteroaryl, moiety having from 1 to about 5 substituents, and more preferably from 1 to about 3 substituents, independently, selected from the group consisting of halogen, cyano, nitro, hydroxyl, $C_1$-$C_6$ alkyl, and $C_1$-$C_6$ alkoxy. Preferred substituents are halogen, hydroxyl, or $C_1$-$C_6$ alkyl.

In some embodiments of the present invention, $R_5$ and $R_6$ are preferably, independently or the same, hydrogen, $C_1$-$C_6$ alkyl, or hydroxyl, and more preferably hydrogen.

In other embodiments, A is preferably an alkylenyl group, —(CH$_2$)$_n$—, where n is 1 to 3, more preferably 1 to 2 and most preferably 2.

In other embodiments, R$_1$ and R$_2$ are, independently, hydrogen or

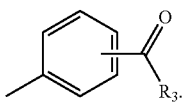

In some embodiments, R$_1$ and R$_2$ are the same. In another embodiment, both R$_1$ and R$_2$ are not hydrogen.

In other embodiments, R$_3$ is independently hydrogen, —OR$_4$, alkyl, aryl, or heteroaryl. In yet other embodiments, R$_3$ is hydrogen, —OR$_4$, or C$_1$ to C$_6$ alkyl.

In other embodiments, R$_4$ is hydrogen, alkyl, aryl, or heteroaryl. In yet other embodiments, R$_4$ is hydrogen or C$_1$ to C$_6$ alkyl, e.g., ethyl.

In other embodiments, R$_1$ and R$_2$ are preferably, independently, hydrogen or

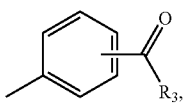

with the proviso that at least one of R$_1$ and R$_2$ is not hydrogen;

R$_3$ is independently hydrogen, —OR$_4$, alkyl, aryl, or heteroaryl, and

R$_4$ is hydrogen, alkyl, aryl, or heteroaryl.

In yet other embodiments, R$_1$ and R$_2$ are preferably, independently, hydrogen or

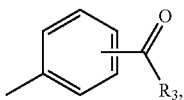

with the proviso that at least one of R$_1$ and R$_2$ is not hydrogen;

R$_3$ is hydrogen, —OR$_4$, or C$_1$ to C$_6$ alkyl; and

R$_4$ is hydrogen or C$_1$ to C$_6$ alkyl.

In further preferred embodiments of the invention,

A is an alkylenyl group having the formula —(CH$_2$)$_n$—;

n is 2;

R$_1$ and R$_2$ are H or

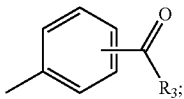

with the proviso that at least one of R$_1$ and R$_2$ is not hydrogen;

R$_3$ is a C$_1$ to C$_3$ alkyl, preferably methyl, or —OR$_4$;

R$_4$ is a C$_1$ to C$_3$ alkyl, preferably, ethyl.

In certain preferred embodiments, R$_5$ and R$_6$ are both hydrogen.

In some preferred embodiments, the carbonyl substituent on the phenyl ring can be at the 2-, 3-, or 4-position of the phenyl ring and, more preferably, at the 3-position of the phenyl ring (such as the first preferred compound below).

Some preferred examples of compounds of the present invention include the following:

diethyl 3,3'-[({2-[8,9-dioxo-2,6-diazabicyclo[5.2.0]non-1(7)-en-2-yl]ethyl}phosphoryl)bis(oxy)]dibenzoate (Example 1);

diethyl 2,2'-[({2-[8,9-dioxo-2,6-diazabicyclo[5.2.0]non-1(7)-en-2-yl]ethyl}phosphoryl)bis(oxy)]dibenzoate;

diethyl 4,4'-[({2-[8,9-dioxo-2,6-diazabicyclo[5.2.0]non-1(7)-en-2-yl]ethyl}phosphoryl)bis(oxy)]dibenzoate;

bis(4-acetylphenyl){2-[8,9-dioxo-2,6-diazabicyclo[5.2.0]non-1(7)-en-2-yl]ethyl}phosphonate;

bis(3-acetylphenyl){2-[8,9-dioxo-2,6-diazabicyclo[5.2.0]non-1(7)-en-2-yl]ethyl}phosphonate;

bis(2-acetylphenyl){2-[8,9-dioxo-2,6-diazabicyclo[5.2.0]non-1(7)-en-2-yl]ethyl}phosphonate;

or a pharmaceutically acceptable salt thereof.

In further embodiments, the invention provides compounds of formula (I), (II), (III), and pharmaceutically acceptable salts thereof, where one of R$_1$ and R$_2$ is hydrogen.

The compounds of this invention may contain asymmetric carbon atoms and/or phosphorus atoms, and thus can give rise to optical isomers and diastereoisomers. While shown without respect to stereochemistry in formula (I), (II) or (III), or a pharmaceutically acceptable salt thereof, the present invention includes such optical isomers and diastereoisomers; as well as the racemic and resolved, enantiomerically pure R and S stereoisomers; as well as other mixtures of the R and S stereoisomers and pharmaceutically acceptable salts thereof.

Where an enantiomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. "Substantially free," as used herein, means that the compound is made up of a significantly greater proportion of one enantiomer. In preferred embodiments, the compound is made up of at least about 90% by weight of a preferred enantiomer. In other embodiments of the invention, the compound is made up of at least about 99% by weight of a preferred enantiomer. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

One skilled in the art will also recognize that it is possible for tautomers to exist of formula (I), (II), (III), and pharmaceutically acceptable salts thereof. The present invention includes all such tautomers even though not shown in formula (I), (II), (III), and pharmaceutically acceptable salts thereof.

The compounds useful in the present invention also include pharmaceutically acceptable salts of the compounds of formula (I), (II), or (III). By "pharmaceutically acceptable salt", it is meant any compound formed by the addition of a pharmaceutically acceptable base and a compound of formula (I), (II), or (III) to form the corresponding salt. By the term "pharmaceutically acceptable" it is meant a substance that is acceptable for use in pharmaceutical applications from a toxicological perspective and does not adversely interact with the active ingredient. Preferably, the pharmaceutically acceptable salts are alkali metal (sodium, potassium, lithium) or alkaline earth metal (calcium, magnesium) salts of the compounds of formula (I), (II), or (III), or salts of the compounds of formula (I), (II), or (III) with pharmaceutically acceptable cations derived from ammonia or a basic amine. Examples of the later include, but are not limited to, ammonium, mono-, di-, or trimethylammonium, mono-, di-, or triethylammonium, mono-, di-, or tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 1-isopropylpyrrolidinium, 1,4-dimethylpiperazinium, 1-n-butylpiperidinium, 2-methylpiperidinium, 1-ethyl-2-methylpiperidinium, mono-, di-, or triethanolammonium, tris-(hydroxymethyl)methylammonium, or phenylmono ethanolammonium.

The compounds of the present invention, including compounds of formula (I), (II), (III), and pharmaceutically acceptable salts thereof, can be prepared according to the following schemes and methods:

$R_5$ and $R_6$ are, independently, hydrogen, alkyl, hydroxyl, alkoxy, or $C_5$ to $C_7$ aryl. Each of the alkyl, alkoxy, and $C_5$ to $C_7$ aryl may optionally be substituted as discussed above.

The anion of the bicyclic intermediate (2) can be formed by contacting (2) with a suitable base, such as a hydride or alkoxide, including, for example, sodium methoxide, potassium t-butoxide, sodium hydride or the like, in a suitable aprotic solvent, such as N,N-dimethylformamide or tetrahydrofuran. The anion is then treated with the phosphonate ester intermediate (3), where preferably $A_1$ is $(CH_2)_2$, but may be $C_2$-$C_4$ alkenyl or $C_2$-$C_4$ alkynyl, and preferably $R_1$ and $R_2$ are:

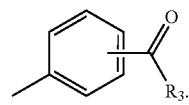

The mixture is stirred at ambient temperature from about 10 hours to about 25 hours, more preferably from about 12 to

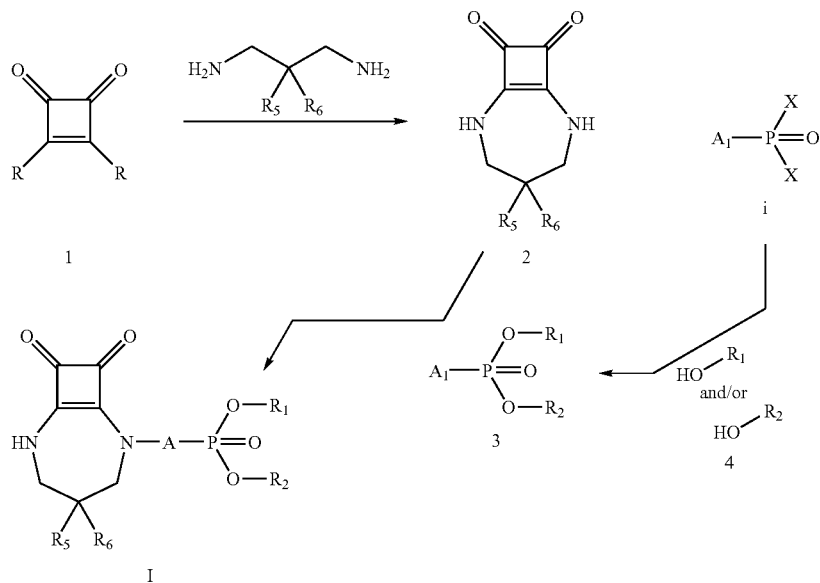

Scheme 1

The compounds of general formula (I) can be conveniently prepared as shown in Scheme 1. Thus, reaction of a diaminoalkane with an dialkoxysquarate (1) in a suitable protic solvent, such as methanol, ethanol and the like, at a temperature ranging from about 0° C. to about 50° C., preferably at a temperature ranging from about 20° C. to about 30° C., provides the bicyclic intermediate of formula (2). By "suitable solvent" it is meant a solvent in which both the amine and the squarate are at least partially soluble and with which both are substantially non-reactive. Typically, the reaction time is about 10 hours to about 25 hours, and more preferably about 12 hours to about 18 hours.

In some preferred embodiments, the diaminopropane is 1,3-diaminopropane. In some preferred embodiments, R is $C_1$ to $C_4$ alkoxy. Most preferably, the dialkoxysquarate is diethoxysquarate, where each R is —OEt. In some embodiments, $R_5$ and $R_6$ are both hydrogen. In further embodiments, about 18 hours. The desired compound of formula (I) is isolated from the reaction mixture using suitable purification techniques, such as flash chromatography or high-pressure liquid chromatography.

The phosphonate ester intermediate (3) can be prepared by alkylation of a compound of formula (4) with a phosphono dihalide (i), where X is a halide, $A_1$ is as defined above, and $R_1$ and $R_2$ are:

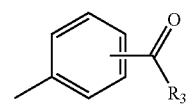

in a suitable aprotic solvent, such as dichloromethane or the like, at temperatures ranging from about 0° C. to about 30° C.

In a preferred embodiment, $A_1$ is $(CH_2)_2$ and X is Cl. The reaction time is from about 10 hours to about 25 hours, and more preferably from about 12 hours to about 16 hours. By "suitable solvent" it is meant a solvent in which both reagents are at least partially soluble and with which both reagents are substantially non-reactive. Preferably an acid scavenger (to react with the acid halide by-product of the reaction), such as an organic amine is optionally added to the reaction mixture in the reaction to form intermediate (3). The organic amine is preferably a secondary or tertiary amine and more preferably a tertiary amine, such as triethylamine.

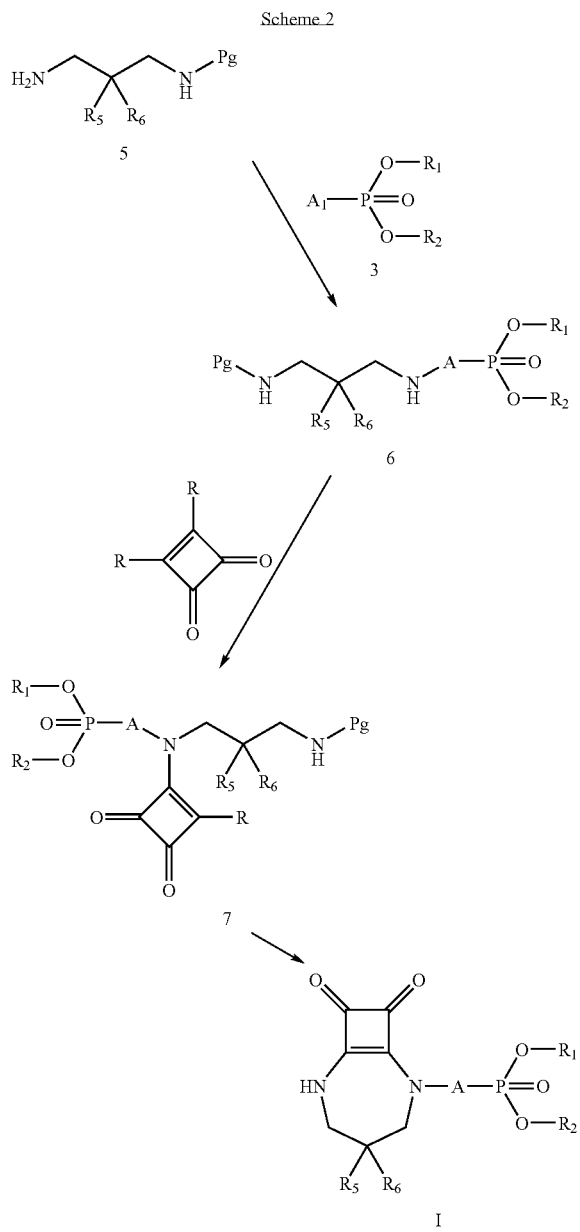

Scheme 2

Alternatively, the compounds of formula (I), (II), (III), and pharmaceutically acceptable salts thereof, can be obtained as shown in Scheme 2 by adding the intermediate (3), one preparation of which is described above, to a mono-protected diaminoalkane (5) at ambient temperature and in a suitable aprotic solvent, such as tetrahydrofuran. The diaminoalkane may be mono-protected using a suitable protecting group Pg, such as t-butoxycarbonyl. The resulting disubstituted diaminoalkane derivative (6) is treated preferably at ambient temperature, with a dialkoxysquarate (1) in a suitable solvent, such as acetonitrile to provide the tri-substituted diaminoalkane derivative (7). The latter (7) is deprotected, for example, using trifluoroacetic acid in a suitable aprotic solvent, such as methylene chloride after which cyclization is accomplished using, for example, an organic base, preferably a tertiary amine, such as triethylamine in a suitable solvent, such as acetonitrile. Those of skill in the art will readily recognize suitable protecting groups which may be used in this synthesis.

More specific syntheses of exemplary compounds of the invention are detailed in the Examples below.

The compounds of the present invention, including compounds of formula (I), (II), (III), and pharmaceutically acceptable salts thereof, when administered to mammals, are NMDA antagonists, and are thus useful for treating a variety of disorders that benefit from inhibiting the NMDA receptor in mammals. By "treat" or "treating," as used herein, it is meant at least partially or completely alleviating, inhibiting, preventing, ameliorating and/or relieving the disorder. For example, "treat" and "treating," as used herein, includes partially or completely alleviating, ameliorating, or relieving the condition in question. Also, for example, "treat" and "treating" is meant to include totally or partially inhibiting (i.e., preventing) the development of pain.

"Mammals," as used herein, refers to warm blooded vertebrate animals, such as humans.

Accordingly, the present invention provides methods for treating conditions in mammals that would benefit from inhibiting the NMDA receptor that includes administering to a mammal in need thereof a therapeutically effective amount of at least one compound of formula (I), (II), (III), and pharmaceutically acceptable salts thereof.

While in no way intending to be bound in theory, it is believed that the compounds of the present invention after administration into a mammal, form the corresponding phosphonic acid (i.e., where $R_1$ and/or $R_2$ are hydrogen in formula (I)). It has surprisingly been discovered that compounds of the present invention relative to such corresponding phosphonic acids have improved bioavailability when administered orally to mammals. Additionally, the compounds of the present invention, after administration into mammals, have a unique affinity and selectivity for certain binding sites on the NMDA receptor. This unique affinity and selectivity is believed to provide effective treatment at lower doses and/or cause fewer side effects at doses to provide the desired treatment. This is particularly evident when the condition being treated is pain.

In other embodiments, the present invention provides methods for treating one or more conditions associated with a glutamate abnormality that includes administering orally to a mammal in need thereof a therapeutically effective amount of at least one compound of formula (I), (II), (III), and pharmaceutically acceptable salts thereof. As used herein, "associated with" refers to conditions directly or indirectly caused by a glutamate abnormality. "Glutamate abnormality" refers to any condition produced by a disease or a disorder in which glutamate and/or its receptors are implicated as a contributing factor to the disease or disorder. Conditions believed to be associated with a glutamate abnormality include, but are not limited to, vascular disorders associated with a glutamate abnormality, such as cerebral vascular disorders including, but not limited to, cerebral ischemia (e.g., stroke) or cerebral infarction resulting in a range of conditions, such as thromboembolic or hemorrhagic stroke, or cerebral vasospasm; cerebral trauma; muscular spasm; convulsive disorders, such as epilepsy or status epilepticus; glaucoma; pain; anxiety disorders, such as panic attack, agoraphobia, panic disorder, specific phobia, social phobia, obsessive compulsive disorder, posttraumatic stress disorder, acute stress disorder, generalized anxiety disorder, separation anxiety disorder, or substance-induced anxiety disorder; mood disorders, such as bipolar disorders (e.g., bipolar I disorder, bipolar II disorder, and cyclothymic disorder), depressive disorders (e.g., major depressive disorder, dysthymic disorder, and substance-induced mood disorder), mood episodes (e.g., major depressive episode, manic episode, mixed episode, and hypomanic episode); schizophrenia; schizophreniform disorder; schizoaffective disorder; cognitive impairment, such as memory loss; and chronic neurodegenerative disorders, such as Parkinson's disease, Huntington's disease, Alzheimer's disease, amyotrophic lateral sclerosis, or chronic dementia related to, for example, Lewy body disease, Alzheimer's disease, fronto temporal dementia, or AIDS. With respect to the mental disorders listed above, such as schizophrenia, mood disorders and anxiety disorders, reference is made to the *Diagnostic and Statistical Manual of Mental Disorders,* 4th edition, Washington, D.C., American Psychiatric Association (1994) for a more complete description of each of the mental disorder.

Additional conditions believed to be related to glutamate abnormalities include inflammatory diseases; hypoglycemia; diabetic end organ complications; cardiac arrest; asphyxia anoxia, such as from near drowning, pulmonary surgery and cerebral trauma; and spinal cord injury. The compounds of the present invention may also be used to treat fibromyalgia, irritable bowel syndrome, and complications from herpes zoster (shingles), such as prevention of post-herpetic neuralgia. The compounds in the present invention may also be used to prevent tolerance to opiate analgesia or to help control symptoms of withdrawal from addictive drugs. Thus, the present invention provides methods for treating each of the aforementioned conditions that includes administering orally to a mammal in need thereof a therapeutically effective amount of at least one compound of formula (I), (II), or (III).

In one preferred embodiment, the compounds useful in the present invention are used to treat pain. The pain may be, for example, acute pain (short duration) or chronic pain (reoccurring or persistent). The pain may also be centralized or peripheral.

Examples of pain that can be acute or chronic and that can be treated in accordance with the methods of the present invention include inflammatory pain, musculoskeletal pain, bony pain, lumbosacral pain, neck or upper back pain, visceral pain, somatic pain, neuropathic pain, cancer pain, pain caused by injury or surgery, such as burn pain or dental pain, or headaches, such as migraines or tension headaches, or combinations of these pains. One skilled in the art will recognize that these pains may overlap one another. For example, a pain caused by inflammation may also be visceral or musculoskeletal in nature.

In a preferred embodiment of the present invention the compounds useful in the present invention, including compounds of formula (I), (II), (III), and pharmaceutically acceptable salts thereof, are administered in mammals to treat chronic pain, such as neuropathic pain associated for example with damage to or pathological changes in the peripheral or central nervous systems; cancer pain; visceral pain associated with for example the abdominal, pelvic, and/or perineal regions or pancreatitis; musculoskeletal pain associated with for example the lower or upper back, spine, fibromyalgia, temporomandibular joint, or myofascial pain syndrome; bony pain associated with for example bone or joint degenerating disorders, such as osteoarthritis, rheumatoid arthritis, or spinal stenosis; headaches such migraine or tension headaches; or pain associated with infections, such as HIV, sickle cell anemia, autoimmune disorders, multiple sclerosis, or inflammation, such as osteoarthritis or rheumatoid arthritis.

In a more preferred embodiment, the compounds useful in this invention, including compounds of formula (I), (II), (III), and pharmaceutically acceptable salts thereof, are used to treat chronic pain that is neuropathic pain, visceral pain, musculoskeletal pain, bony pain, cancer pain or inflammatory pain or combinations thereof, in accordance with the methods described herein. Inflammatory pain can be associated with a variety of medical conditions, such as osteoarthritis, rheumatoid arthritis, surgery, or injury. Neurophathic pain includes peripheral neuropathic pain, central neuropathic pain or combinations thereof. Neuropathic pain may be associated with for example diabetic neuropathy, post-herpetic neuralgia, trigeminal neuralgia, complex regional pain syndrome, lumbar or cervical radiculopathies, fibromyalgia, glossopharyngeal neuralgia, reflex sympathetic dystrophy, causalgia, thalamic syndrome, nerve root avulsion, monoclonal gammopathy of undetermined significance (MGUS) neuropathy, sarcoid polyneuropathy, HIV-related neuropathy arising from a variety of causes, such as from medication used to treat HIV, peripheral neuropathy, such as peripheral neuropathy with connective tissue disease, paraneoplastic sensory neuropathy, familial amyloid polyneuropathy, acquired amyloid polyneuropathy, inherited neuropathy, neuropathy with renal failure, hereditary sensory autonomic neuropathy, Fabry's disease, Celiac disease or nerve damage cause by injury resulting in peripheral and/or central sensitization, such as phantom limb pain, reflex sympathetic dystrophy or postthoracotomy pain, cancer including neuropathies caused by chemotherapy agents or other agents used to treat the disease, chemical injury, toxins, such as arsenic neuropathy, nutritional deficiencies, or viral or bacterial infections, such as shingles or HIV-related neuropathy, or combinations thereof. The methods of use for compounds of this invention further include treatments in which the neuropathic pain is a condition secondary to metastatic infiltration, adiposis dolorosa, burns, or central pain conditions related to thalamic conditions.

Neuropathic pains described above may also be, in some circumstances, classified as "painful small fiber neuropathies", such as idiopathic small-fiber painful sensory neuropathy, or "painful large fiber neuropathies", such as demylinating neuropathy or axonal neuropathy, or combinations thereof. Such neuropathies are described in more detail, for example, in the J. Mendell, et al., *N. Engl. J. Med.* 2003, 348:1243-1255, which is hereby incorporated by reference in its entirety.

As mentioned previously, the methods of the present invention may be used to treat pain that is somatic and/or visceral in nature. For example, somatic pain that can be treated in accordance with the methods of the present invention include pains associated with structural or soft tissue injury experienced during surgery, dental procedures, burns, or traumatic body injuries. Examples of visceral pain that can be treated in accordance with the methods of the present invention include those types of pain associated with or resulting from maladies of the internal organs, such as ulcerative colitis, irritable bowel syndrome, irritable bladder, Crohn's disease, rheumatologic (arthralgias), tumors, gastritis, pancreatitis, infections of the organs, or biliary tract disorders, or combinations thereof. One skilled in the art will also recognize that the pain treated according to the methods of the present invention may also be related to conditions of hyperalgesia, allodynia, or both. Additionally, the chronic pain may be with or without peripheral or central sensitization.

The compounds useful in this invention, including compounds of formula (I), (II), (III), and pharmaceutically acceptable salts thereof, may also be used to treat acute and/or chronic pains associated with female conditions, which may also be referred to as female-specific pain. Such groups of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes.

As mentioned previously, the term "treat" or "treating", as used herein, is also meant to include totally or partially inhibiting (i.e., preventing) the development of pain. Thus, compounds of the present invention may be administered to a mammal prior to the mammal experiencing pain to partially or totally inhibit the development of pain.

In some embodiments, the compounds useful in the present invention, including compounds of formula (I), (II), (III), and pharmaceutically acceptable salts thereof, may be administered prior to or during a surgical procedure to partially or totally inhibit development of pain associated with the surgical procedure. In a preferred embodiment, the compounds useful in the present invention are preferably administered from about 0.25 hours to about 4 hours prior to the surgical procedure. For surgical procedures of greater duration, dosing is preferably repeated during the surgical procedure about every time interval corresponding to the in vivo half life ($T_{1/2}$) of the compound.

In another embodiment of the present invention, it has been found that administering compounds useful in the present invention, including compounds of formula (I), (II), (III), and pharmaceutically acceptable salts thereof, prior to a surgical procedure may increase the potency and/or effectiveness of other pain relieving agents, such as opioid analgesics (e.g., morphine) that are administered after the surgical procedure, and/or may reduce the amount of pain relieving agent needed to treat the post operative surgical pain. Thus, the present invention provides methods of treating pain associated with a surgical procedure that includes administering prior to or during the surgical procedure a compound useful in the present invention, and administering after or during a surgical procedure a therapeutically effective amount of at least one pain relieving agent, such as an opioid analgesic. In preferred embodiments, compounds of the present invention may be administered to a mammal also after the surgical procedure, preferably in combination with the one or more pain relieving agents. "Surgical procedure," as used herein, includes all therapeutic, diagnostic, and/or cosmetic manipulations, disruptions, movements, radiations, ablations, chemical or physical alterations in any tissue, organ, or body system including but not limited to blood, blood vessels, fat, skin, connective tissue, muscle, internal organs, glands, bone, cartilage, nerve, marrow, fascia, meninges, sensory apparatus, brain or spinal cord. Surgical procedure includes, for example, procedures performed on mammals using more recent surgical techniques, such as laser, ultrasound, and radiation in addition to more traditional techniques.

In another embodiment, the compounds useful in the present invention, including compounds of formula (I), (II), (III), and pharmaceutically acceptable salts thereof, may be administered to totally or partially inhibit a neuropathic pain condition from developing. For example, compounds of the present invention may be administered to a mammal that is at risk for developing a neuropathic pain condition, such as a mammal that has contracted shingles or a mammal that is being treated for cancer.

The compounds of the present invention can be administered in any way known to those skilled in the art, including for example, by oral or parenteral administration, such as by intramuscular, intraperitoneal, epidural, intrathecal, intravenous, subcutaneous, intramucosal, such as sublingual or intranasal, vaginal, rectal or transdermal administration. In a preferred embodiment of the present invention, the compounds of the present invention are administered orally, intramucosally or intravenously.

The compounds of the present invention, including compounds of formula (I), (II), (III), and pharmaceutically acceptable salts thereof, are administered in a therapeutically effective amount to the mammal needing treatment. As used herein "a therapeutically effective amount" is at least the minimal amount of the compound or a pharmaceutically acceptable salt form thereof, that treats the condition in question in a mammal. The therapeutically effective amount will depend on such variables as the particular composition used, the route of administration, the severity of the symptoms, and the particular patient being treated. To determine the therapeutically effective amount of the compound to be administered, the physician may, for example, evaluate the effects of a given compound of formula (I), (II), (III), and pharmaceutically acceptable salts thereof, in the patient by incrementally increasing the dosage until the desired symptomatic relief level is achieved. The continuing dose regimen may then be modified to achieve the desired result. For example, in the case of an oral dosage, preferably the compounds of the present invention are incrementally increased in a patient in an amount of from 3 mg/kg to 1000 mg/kg until the desired symptomatic relief level is achieved. The continuing dose regimen may then be modified to achieve the desired result, with the range for oral dosage being preferably from about 20 mg/day to about 1200 mg/day. Similar techniques may be followed by determining the effective dose range for other administration routes, such as by intravenous or intramuscular routes based on bioavailability data.

In another embodiment of the present invention, the compounds of the present invention, including compounds of formula (I), (II), (III), and pharmaceutically acceptable salts thereof, may be administered to a mammal with one or more other pharmaceutical active agents, such as those agents being used to treat any other medical condition present in the mammal. Examples of such pharmaceutical active agents include pain relieving agents, anti-angiogenic agents, anti-neoplastic agents, anti-diabetic agents, anti-infective agents, or gastrointestinal agents, or combinations thereof.

The one or more other pharmaceutical active agents may be administered in a therapeutically effective amount simultaneously (such as individually at the same time, or together in a pharmaceutical composition), and/or successively with one or more compounds of the present invention, including compounds of formula (I), (II), (III), and pharmaceutically acceptable salts thereof.

The method of administration of the other pharmaceutical active agent may be the same or different from the route of administration used for the compounds of the present invention. For example, the other pharmaceutical active agents may be administered by oral or parental administration, such as for example, by intramuscular, intraperitoneal, epidural, intrathecal, intravenous, intramucosal, such as by intranasal or sublingual, subcutaneous or transdermal administration. The preferred administration route will depend upon the particular pharmaceutical active agent chosen and its recommended administration route(s) known to those skilled in the art.

A more complete listing of pharmaceutical active agent can be found in the *Physicians' Desk Reference,* 55th Edition, 2001, published by Medical Economics Co., Inc., Montvale, N.J. Each of these agents may be administered according to the therapeutically effective dosages and regimens known in the art, such as those described for the products in the *Physicians' Desk Reference,* 55th Edition, 2001, published by Medical Economics Co., Inc., Montvale, N.J.

In a preferred embodiment of the present invention, the compounds of the present invention, including compounds of formula (I), (II), (III), and pharmaceutically acceptable salts thereof, may be administered to a mammal with one or more other pain relieving agents to treat pain in a mammal. By "pain relieving agents" it is meant any agent that directly or indirectly treats pain symptoms. Examples of indirect pain relieving agents include for example anti-inflammatory agents, such as anti-rheumatoid agents.

The one or more other pain relieving agents may be administered simultaneously (such as individually at the same time, or together in a pharmaceutical composition), and/or successively with the compounds of the present invention. Preferably, the compounds of the present invention and the one or more pain relieving agents are administered in a manner so that both are present in the mammal body for a certain period of time to treat pain.

The method of administration of the other pain relieving agent may be the same or different from the route of administration used for the compound of the present invention. For example, opioids are preferably administered by oral, intravenous, or intramuscular administration routes.

One skilled in the art will recognize that the dosage of the other pain relieving agent administered to the mammal will depend on the particular pain relieving agent in question and the desired administration route. Accordingly, the other pain relieving agent may be dosed and administered according to those practices known to those skilled in the art, such as those disclosed in references, such as the *Physicians' Desk Reference,* 55th Edition, 2001, published by Medical Economics Co., Inc., Montvale, N.J.

Examples of pain relieving agents that may be administered with the compound of the present invention, including compounds of formula (I), (II), (III), and pharmaceutically acceptable salts thereof, include analgesics, such as non-narcotic analgesics or narcotic analgesics; anti-inflammatory agents, such as non-steroidal anti-inflammatory agents (NSAID), steroids or anti-rheumatic agents; migraine preparations, such as beta adrenergic blocking agents, ergot derivatives, or isometheptene; tricyclic antidepressants, such as amitryptyline, desipramine, or imipramine; anti-epileptics, such as gabapentin, carbamazepine, topiramate, sodium valproate or phenytoin; $\alpha_2$ agonists; or selective serotonin reuptake inhibitors/selective norepinepherine uptake inhibitors, or combinations thereof. One skilled in the art will recognize that some agents described hereinafter act to relieve multiple conditions, such as pain and inflammation, while other agents may just relieve one symptom, such as pain. A specific example of an agent having multiple properties is aspirin, where aspirin is anti-inflammatory when given in high doses, but at lower doses is just an analgesic. The pain relieving agent may include any combination of the aforementioned agents, for example, the pain relieving agent may be a non-narcotic analgesic in combination with a narcotic analgesic.

Non-narcotic analgesics useful in the present invention include, for example, salicylates, such as aspirin, ibuprofen (MOTRIN®, ADVIL®), ketoprofen (ORUDIS®), naproxen (NAPROSYN®), acetaminophen, indomethacin or combinations thereof. Examples of narcotic analgesic agents that may be used in combination with the cyclobutene derivatives include opioid analgesics, such as fentenyl, sufentanil, morphine, hydromorphone, codeine, oxycodone, buprenorphine or pharmaceutically acceptable salts thereof or combinations thereof. Examples of anti-inflammatory agents that may be used in combination with the cyclobutene derivatives include but are not limited to aspirin; ibuprofen; ketoprofen; naproxen; etodolac (LODINE®); COX-2 inhibitors, such as celecoxib (CELEBREX®), rofecoxib (VIOXX®), valdecoxib (BEXTRA®), parecoxib, etoricoxib (MK663), deracoxib, 2-(4-ethoxy-phenyl)-3-(4-methanesulfonyl-phenyl)-pyrazolo[1,5-b]pyridazine, 4-(2-oxo-3-phenyl-2,3-dihydrooxazol-4-yl)benzenesulfonamide, darbufelone, flosulide, 4-(4-cyclohexyl-2-methyl-5-oxazolyl)-2-fluorobenzenesulfonamide), meloxicam, nimesulide, 1-methyl-sulfonyl-4-(1,1-dimethyl-4-(4-fluorophenyl)cyclopenta-2,4-dien-3-yl)benzene, 4-(1,5-Dihydro-6-fluoro-7-methoxy-3-(trifluoromethyl)-(2)-benzothiopyrano(4,3-c)pyrazol-1-yl) benzenesulfonamide, 4,4-dimethyl-2-phenyl-3-(4-methylsulfonyl)phenyl)cyclo-butenone, 4-Amino-N-(4-(2-fluoro-5-trifluoromethyl)-thiazol-2-yl)-benzene sulfonamide, 1-(7-tert-butyl-2,3-dihydro-3,3-dimethyl-5-benzo-furanyl)-4-cyclopropyl butan-1-one, or their physiologically acceptable salts, esters or solvates; sulindac (CLINORIL®); diclofenac (VOLTAREN®); piroxicam (FELDENE®); diflunisal (DOLOBID®), nabumetone (RELAFEN®), oxaprozin (DAYPRO®), indomethacin (INDOCIN®); or steroids, such as PEDIAPED® prednisolone sodium phosphate oral solution, SOLU-MEDROL® methylprednisolone sodium succinate for injection, PRELONE® brand prednisolone syrup.

Further examples of anti-inflammatory agents preferably used for treating rheumatoid arthritis include naproxen, which is commercially available in the form of EC-NAPROSYN® delayed release tablets, NAPROSYN®, ANAPROX® and ANAPROX® DS tablets and NAPROSYN® suspension from Roche Labs, CELEBREX® brand of celecoxib tablets, VIOXX® brand of rofecoxib, CELESTONE® brand of betamethasone, CUPRAMINE® brand penicillamine capsules, DEPEN® brand titratable penicillamine tablets, DEPO-MEDROL brand of methylprednisolone acetate injectable suspension, ARAVA™ leflunomide tablets, AZULFIDIINE EN-tabs® brand of sulfasalazine delayed release tablets, FELDENE® brand piroxicam capsules, CATAFLAM® diclofenac potassium tablets, VOLTAREN® diclofenac sodium delayed release tablets, VOLTAREN®-XR diclofenac sodium extended release tablets, or ENBREL® etanerecept products.

Examples of other agents used to treat inflammations, especially rheumatoid arthritis include immunosuppressants, such as GENGRAF™ brand cyclosporine capsules, NEORAL® brand cyclosporine capsules or oral solution, or IMURAN® brand azathioprine tablets or IV injection; INDOCIN® brand indomethacin capsules, oral suspension or suppositories; PLAQUENIL® brand hydroxychloroquine sulfate; or REMICADE® infliximab recombinant for IV injection; or gold compounds, such as auranofin or MYO-CHRISYINE® gold sodium thiomalate injection.

In a preferred embodiment of the present invention, at least one compound of the present invention is administered with at least one opioid analgesic in accordance with the methods previously described herein to treat pain. It has been found that the compounds of the present invention, when administered with at least one opioid analgesic, such as morphine, have such beneficial effects as synergistically decreasing pain perception, increasing the duration of pain relief, and/or decreasing adverse side effects.

The compounds of the present invention, including compounds of formula (I), (II), (III), and pharmaceutically acceptable salts thereof, may be administered neat (i.e., as is) or in a pharmaceutical composition containing at least one pharmaceutically acceptable carrier. Thus, the present invention also provides pharmaceutical compositions containing a pharmaceutically effective amount of at least one compound of formula (I), (II), (III), and pharmaceutically acceptable salts thereof, and at least one pharmaceutically acceptable carrier. Preferred compounds to be present in the pharmaceutical compositions of the present invention include those compounds of formula (I), (II), (III), and pharmaceutically acceptable salts thereof previously described as being preferred. Pharmaceutically acceptable carriers are those that are compatible with the other ingredients in the formulation and biologically acceptable. The pharmaceutical compositions may be administered to a mammal to treat a variety of conditions that would benefit from inhibiting the NMDA receptor as previously described herein.

Pharmaceutical compositions useful in the present invention may be in any form known to those skilled in the art, such as in liquid or solid form. The proportion of ingredients will depend on such factors as the solubility and chemical nature of the compound of formula (I), (II), (III), and pharmaceutically acceptable salts thereof, and the chosen route of administration. Such compositions are prepared in accordance with acceptable pharmaceutical procedures, such as described in *Remington's Pharmaceutical Sciences,* 17th edition, ed. Alfonoso R. Gennaro, Mack Publishing Company, Easton, Pa. (1985).

Pharmaceutical compositions, in addition to containing a therapeutically effective amount of one or more compounds of the present invention and a pharmaceutically acceptable carrier may include one or more other ingredients known to those skilled in the art for formulating pharmaceutical compositions. Such ingredients include for example, flavoring agents, lubricants, solubilizers, suspending agents, fillers, glidants, compression aids, binders, tablet-disintegrating agents, encapsulating materials, emulsifiers, buffers, preservatives, sweeteners, thickening agents, coloring agents, viscosity regulators, stabilizers or osmo-regulators, or combinations thereof.

Solid pharmaceutical compositions preferably contain one or more solid carriers, and optionally one or more other additives, such as flavoring agents, lubricants, solubilizers, suspending agents, fillers, glidants, compression aids, binders or tablet-disintegrating agents or an encapsulating material. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes or ion exchange resins, or combinations thereof. In powder pharmaceutical compositions, the carrier is preferably a finely divided solid which is in admixture with the finely divided active ingredient. In tablets, the active ingredient is mixed with a carrier having the necessary compression properties in suitable proportions, and optionally, other additives, and compacted into the desired shape and size. Solid pharmaceutical compositions, such as powders and tablets, preferably contain up to 99% of the active ingredient.

Liquid pharmaceutical compositions preferably contain one or more compounds of the present invention and one or more liquid carriers to form for example solutions, suspensions, emulsions, syrups, elixirs, or pressurized compositions. Pharmaceutically acceptable liquid carriers include for example water, organic solvent, pharmaceutically acceptable oils or fat, or combinations thereof. The liquid carrier can contain other suitable pharmaceutical additives, such as solubilizers, emulsifiers, buffers, preservatives, sweeteners, flavoring agents, suspending agents, thickening agents, colors, viscosity regulators, stabilizers or osmo-regulators, or combinations thereof.

Examples of liquid carriers suitable for oral or parenteral administration include water (preferably containing additives, such as cellulose derivatives, such as sodium carboxymethyl cellulose), alcohols or their derivatives (including monohydric alcohols or polyhydric alcohols, such as glycols) or oils (e.g., fractionated coconut oil and arachis oil). For parenteral administration, the carrier can also be an oily ester, such as ethyl oleate and isopropyl myristate. The liquid carrier for pressurized compositions can be halogenated hydrocarbons or other pharmaceutically acceptable propellant.

Liquid pharmaceutical compositions which are sterile solutions or suspensions can be administered parenterally, for example by, intramuscular, intraperitoneal, epidural, intrathecal, intravenous or subcutaneous injection. Pharmaceutical compositions for oral or transmucosal administration may be either in liquid or solid composition form.

The compounds of this invention, including compounds of formula (I), (II), (III), and pharmaceutically acceptable salts thereof, may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms, such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semipermeable membrane covering a reservoir containing the active ingredient with or without a carrier, or a matrix containing the active ingredient. Other occlusive devices are known in the literature.

In another embodiment of the present invention, the pharmaceutical composition, in addition to containing a compound of the present invention, including compounds of formula (I), (II), (III), and pharmaceutically acceptable salts thereof, may also contain a therapeutically effective amount of one or more pain relieving agents as previously described herein, and/or a therapeutically effective amount one or more other pharmaceutical active agents as previously described herein. Thus, the present invention also provides a pharmaceutical composition containing a therapeutically effective amount of at least one compound of the present invention and a therapeutically effective amount of at least one pharmaceutical active agent, such as a pain relieving agent as previously described. For example, the pharmaceutical composition may contain one or more pain relieving agents that includes an opioid analgesic.

Preferably, the pharmaceutical composition is in unit dosage form, such as tablets or capsules. In such form, the composition is sub-divided in unit dose containing appropriate quantities of the active ingredient, including compounds of formula (I), (II), (III), and pharmaceutically acceptable salts thereof. The unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

Thus, the present invention also provides a pharmaceutical composition in unit dosage form that contains a therapeutically effective unit dosage of at least one compound of the present invention. As one skilled in the art will recognize, the preferred unit dosage will depend on for example the method of administration and the condition being treated. For example, a unit dosage for oral administration for treating pain preferably ranges from about 20 mg to about 300 mg of the compound of the present invention.

The present invention also provides a therapeutic package for dispensing the compound of the present invention, including compounds of formula (I), (II), (III), and pharmaceutically acceptable salts thereof, to a mammal being treated. Preferably, the therapeutic package contains one or more unit dosages of the compound of the present invention and a container containing the one or more unit dosages and labeling directing the use of the package for treating the condition, such as pain, in a mammal. In a preferred embodiment, the unit dose is in tablet or capsule form. In a preferred embodiment, each unit dosage is in a therapeutically effective amount for treating pain.

EXAMPLES

The following describes syntheses of exemplary compounds of Formula I depicted by Scheme 1a, which is adapted from general Scheme 1 above.

Synthesis of Intermediates

Dichloro Vinylphosphonate (i)

Trimethylsilyl bromide (150 mmol, 23 g) was added dropwise over 20 minutes to a solution of dimethyl vinylphosphonate (40 mmol, 6.12 g) in methylene chloride (100 mL) under stirring and dry nitrogen at ambient temperature. The reaction mixture was stirred for 3 hours at ambient temperature, evaporated under vacuo to dryness and the residue stripped two times with toluene (2×30 mL). The resultant faintly orange colored oil was subjected to vacuum (1 Torr) overnight to afford 10 g (~100%) of the silyl ester. The silyl ester (39.6 mmol, 10 g) was dissolved in methylene chloride (20 mL) and dropwise added to a suspension of phosphorous pentachloride (80 mmol, 16.7 g) in methylene chloride (100 mL) under stirring and exclusion of moisture. A mild exothermic reaction was noticed and the mixture was stirred for about one hour. The resulting clear solution was evaporated in vacuo and the residue distilled under reduced pressure. The fraction distilling at 63-66° C. and 16 Torr gave 5.2 g (90%) of the title compound as colorless oil.

Diethyl 3,3'-[(vinylphosphoryl)bis(oxy)] dibenzoate (3)

A solution containing ethyl-3-hydroxybenzoate (8 mmol, 1.329 g) and triethylamine (8.3 mmol, 829 mg) in methylene chloride (50 mL) was added dropwise at 0° C. under stirring to a solution of dichloro vinylphosphonate (4 mmol, 0.58 g) in methylene chloride (20 mL). The reaction mixture was stirred at ambient temperature for 24 hours, washed twice with water (40 mL each). The separated organic layer was washed with brine, dried over magnesium sulfate, filtered and evaporated to dryness in vacuo to yield 1.61 g (86-99%) of the desired title compound. MS (APPI+): m/e 405 [M+H]+.

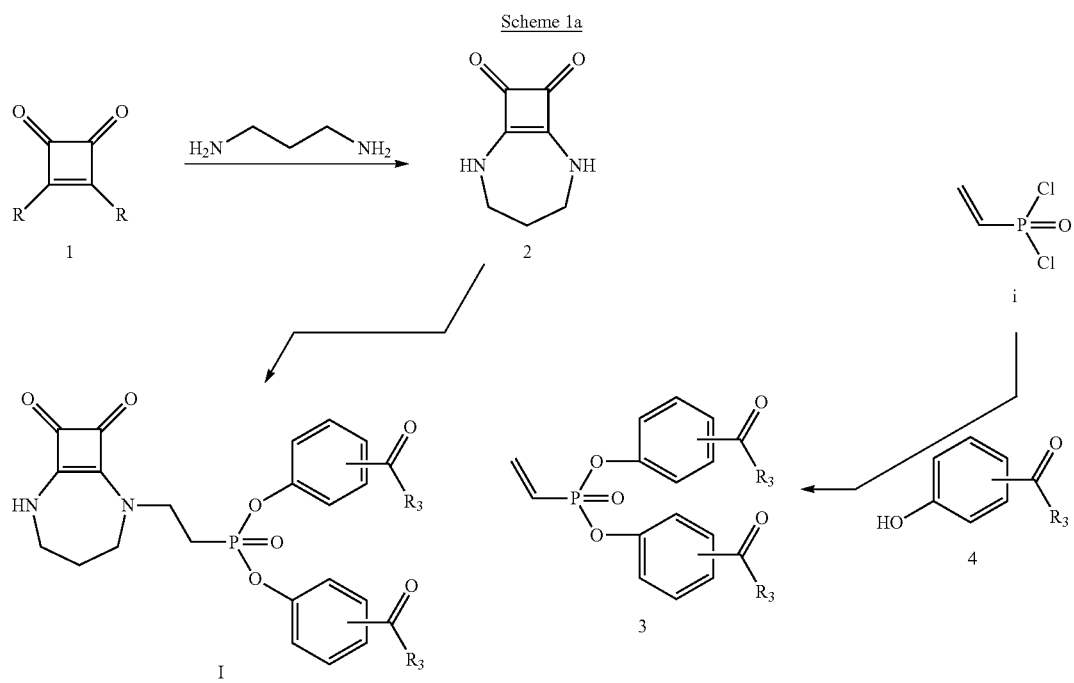

Scheme 1a 2.6-Diaza-bicyclo[5.2.0]non-1(7)-ene-8,9-dione (2)

A solution of 3,4-diethoxy-3-cyclobutene-1,2-dione (20 mmol, 3.4 g) in methanol (80 mL) and a solution of 1,3-diaminopropane (30 mmol, 2.23 g) in //methanol (80 mL) were added dropwise in a parallel fashion over 10 minutes under dry nitrogen at ambient temperature to methanol (130 mL) under vigorous stirring. Stirring was continued overnight after which the precipitated product was filtered and washed with ice-cold methanol (10 mL). The obtained faintly yellowish powder was dried in vacuum (1 Torr) to yield 2.9 g (88-95%) of the desired title compound; mp 335° C. MS (ES−): m/e 151.1 [M−H]⁻.

Example 1

Diethyl 3,3'-[({2-[8,9-dioxo-2,6-diazabicyclo[5.2.0]non-1(7)-en-2-yl]ethyl}phosphoryl)bis(oxy)]dibenzoate

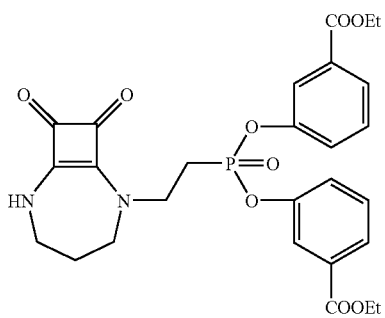

A suspension of 2.6-diaza-bicyclo[5.2.0]non-1(7)-ene-8,9-dione (2) (4 mmol, 608 mg) in N,N-dimethylformamide (60 mL) was treated under dry nitrogen and under stirring with 60% sodium hydride in oil (4.1 mmol, 164 mg). After 30 minutes at ambient temperature the yellow reaction mixture was cooled to 0° C. and a solution of diethyl 3,3'-[(vinylphosphoryl)bis(oxy)]dibenzoate (3) (4 mmol, 1.618 g) in N,N-dimethylformamide (30 mL) was added at once under vigorous stirring. The reaction mixture was then stirred at ambient temperature overnight, concentrated in vacuo and the residue partitioned between 5% aqueous ammonium chloride solution and ethyl acetate (2×60 mL). The organic layers were washed with brine, dried over magnesium sulfate, filtered and evaporated to dryness. The residue (>1.5 g) was flash chromatographed on silica gel (60 g). Elution with 2% methanol in chloroform afforded 600 mg (27%) of the desired title compound as a white powder; mp 116-7° C. MS (ES+): m/e 557.2 [M+H]⁺.

Example 2

Diethyl 2,2'-[({2-[8,9-dioxo-2,6-diazabicyclo[5.2.0]non-1(7)-en-2-yl]ethyl}phosphoryl)bis(oxy)]dibenzoate

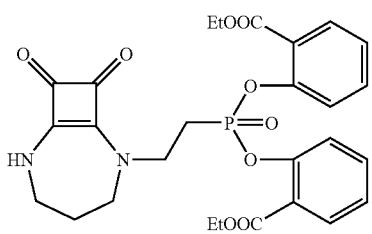

This compound is prepared in accordance with the synthesis of Example 1 but starting from diethyl 2,2'-[(vinylphosphoryl)bis(oxy)]dibenzoate.

Example 3

Diethyl 4,4'-[({2-[8,9-dioxo-2,6-diazabicyclo[5.2.0]non-1(7)-en-2-yl]ethyl}phosphoryl)bis(oxy)]dibenzoate

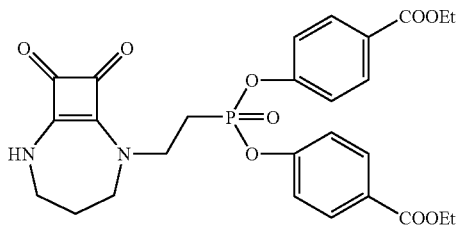

This compound is prepared in accordance with the synthesis of example 1 but starting from diethyl 4,4'-[(vinylphosphoryl)bis(oxy)]dibenzoate.

Example 4

Bis(4-acetylphenyl){2-[8,9-dioxo-2,6-diazabicyclo[5.2.0]non-1(7)-en-2-yl]ethyl}phosphonate

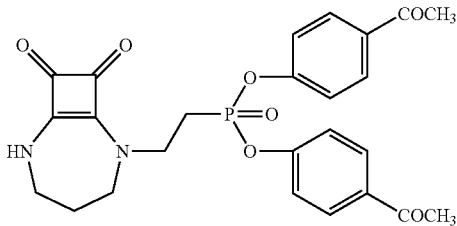

This compound is prepared in accordance with the synthesis of example 1 but starting from vinyl-phosphonic acid bis-(4-acetyl-phenyl)ester.

Example 5

Bis(3-acetylphenyl){2-[8,9-dioxo-2,6-diazabicyclo[5.2.0]non-1(7)-en-2-yl]ethyl}phosphonate

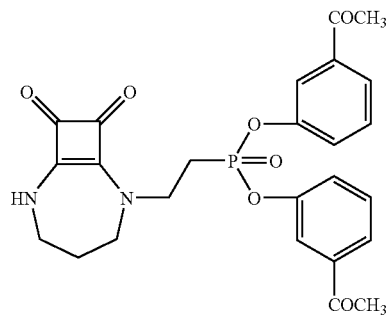

This compound is prepared in accordance with the synthesis of Example 1 but starting from vinyl-phosphonic acid bis-(3-acetyl-phenyl)ester.

Example 6

Bis(2-acetylphenyl){2-[8,9-dioxo-2,6-diazabicyclo[5.2.0]non-1(7)-en-2-yl]ethyl}phosphonate

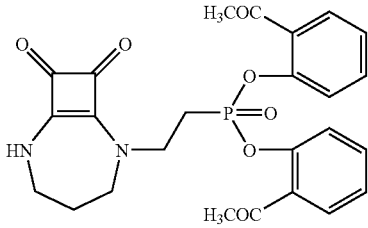

This compound is prepared in accordance with the synthesis of Example 1 but starting from vinyl-phosphonic acid bis-(2-acetyl-phenyl)ester.

Brief Description of Biological Test Procedure(s) and Summary of Results

Example 1 was synthesized and subjected to testing as described below.

Subjects

Individually housed Spraque-Dawley rats had free access to rat chow and water. A 12-h light/12-h dark cycle was in effect (lights on from 6:00 am to 6:00 pm). Animal maintenance and research were conducted in accordance with the guidelines provided by the National Institutes of Health Committee on Laboratory Animal Resources. These subjects were used in the tests below.

Procedure—Prostaglandin E$_2$-Induced Thermal Hypersensitivity:

The terminal 10 cm of the tail (rat) was placed into a thermos bottle containing water warmed to 38, 42, 46, 50 or 54° C. The latency in seconds for the animal to remove the tail from the water was used as a measure of nociception. If the animal did not remove the tail within 20 sec, the experimenter removed the tail and a maximum latency of 20 sec was recorded.

Following the assessment of baseline thermal sensitivity, thermal hypersensitivity was produced by a 50 µL injection of 0.1 mg of prostaglandin E$_2$ (PGE$_2$) into the terminal 1 cm of the tail. Temperature-effect curves were generated before (baseline) and 30 minutes after the PGE$_2$ injection. Previous studies in other species (e.g., monkeys; Brandt, et al., *J. Pharmacol. Exper. Ther.* 296:939, 2001) and results from the current study demonstrate that PGE$_2$ produces a dose- and time-dependent thermal hypersensitivity that peaks 15 min after injection and dissipates after 2 hours.

The ability of the compounds to reverse PGE$_2$-induced thermal hypersensitivity was assessed using a single dose time-course procedure. Under this procedure, a single dose of the compound to be tested was administered orally (PO) 10, 30, 100 or 300 min before the injection of PGE$_2$. Tactile sensitivity was assessed 30 min after PGE$_2$ injection.

Data Analysis—The temperature that produced a half-maximal increase in the tail-withdrawal latency (i.e., T$_{10}$) was calculated from each temperature-effect curve. The T$_{10}$ was determined by interpolation from a line drawn between the point above and the point below 10 sec on the temperature-effect curve. For these studies, thermal hypersensitivity was defined as a leftward shift in the temperature-effect curve and a decrease in the T$_{10}$ value. Reversal of thermal hypersensitivity was defined as a return to baseline of the temperature-effect curve and the T$_{10}$ value and was calculated according to the following equation:

$$\%MPE = \frac{(T_{10}^{drug+PGE2}) - (T_{10}^{PGE2})}{(T_{10}^{baseline}) - (T_{10}^{PGE2})} \times 100$$

in which T$_{10}^{drug+PGE2}$ is the T$_{10}$ after a drug in combination with PGE$_2$, T$_{10}^{PGE2}$ is the T$_{10}$ after PGE$_2$ alone, and T$_{10}^{baseline}$ is the T$_{10}$ under control conditions. A % MPE value of 100 indicates a complete return to the baseline thermal sensitivity observed without the PGE$_2$ injection. A value of greater than 100% indicates that the compound tested reduced thermal sensitivity more than the baseline thermal sensitivity without the PGE$_2$ injection.

Results: Example 1 of the present invention was effective in reversing PGE$_2$-induced thermal hypersensitivity by 40% at a dose of 10 mg/kg p.o.

When ranges are used herein for physical properties, such as molecular weight, or chemical properties, such as chemical formulae, all combinations and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method for treating pain in a mammal, comprising the step of:
   administering to said mammal a therapeutically effective amount of at least one compound of formula (I) or a pharmaceutically acceptable salt thereof:

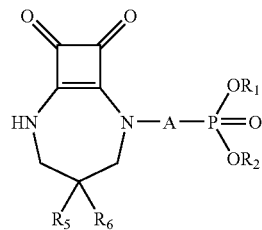

(I)

wherein;

A is alkenyl of 1 to 4 carbon atoms, or alkenylenyl of 2 to 4 carbon atoms;

R$_1$ and R$_2$ are, independently, hydrogen, or C$_5$ to C$_7$ aryl optionally substituted with 1 to 2 substituents, independently, selected from the group consisting of —C(O)R$_3$, halogen, cyano, nitro, hydroxyl group, C$_1$-C$_6$ alkyl group, and C$_1$-C$_6$ alkoxy group, with the proviso that at least one of R$_1$ and R$_2$ is not hydrogen;

R$_3$ is, independently, hydrogen, —OR$_4$, alkyl, aryl, or heteroaryl,

R$_4$ is hydrogen, alkyl, aryl, or heteroaryl,

R$_5$ and R$_6$ are, independently, hydrogen, alkyl, OH, alkoxy, or C$_5$ to C$_7$ aryl;

wherein any R$_3$ to R$_6$ group having an aryl or heteroaryl moiety can optionally be substituted on the aryl or heteroaryl moiety with 1 to about 5 substituents, independently, selected from the group consisting of halogen, cyano, nitro, hydroxyl, C$_1$-C$_6$ alkyl, and C$_1$-C$_6$ alkoxy.

* * * * *